(12) United States Patent
Zhang et al.

(10) Patent No.: US 10,035,837 B2
(45) Date of Patent: *Jul. 31, 2018

(54) WATER SOLUBLE MEMBRANE PROTEINS AND METHODS FOR THE PREPARATION AND USE THEREOF

(71) Applicant: Massachusetts Institute of Technology, Cambridge, MA (US)

(72) Inventors: Shuguang Zhang, Lexington, MA (US); Alexander Rich, Cambridge, MA (US); Karolina Corin, Cambridge, MA (US); Lotta Tolstoy Tegler, Linkoping (SE)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/078,036

(22) Filed: Mar. 23, 2016

(65) Prior Publication Data

US 2016/0264640 A1    Sep. 15, 2016

Related U.S. Application Data

(63) Continuation of application No. 14/105,252, filed on Dec. 13, 2013, now Pat. No. 9,309,302, which is a continuation of application No. 13/403,725, filed on Feb. 23, 2012, now Pat. No. 8,637,452.

(60) Provisional application No. 61/445,740, filed on Feb. 23, 2011.

(51) Int. Cl.
| | |
|---|---|
| C07K 14/705 | (2006.01) |
| C07K 14/715 | (2006.01) |
| G01N 33/68 | (2006.01) |
| A61K 38/17 | (2006.01) |
| A61K 38/00 | (2006.01) |

(52) U.S. Cl.
CPC ............ *C07K 14/705* (2013.01); *A61K 38/17* (2013.01); *A61K 38/177* (2013.01); *A61K 38/1793* (2013.01); *C07K 14/7158* (2013.01); *G01N 33/6863* (2013.01); *A61K 38/00* (2013.01)

(58) Field of Classification Search
CPC ...... A61K 38/00; A61K 38/17; A61K 38/177; A61K 38/1793; C07K 14/705; C07K 14/7158; G01N 33/6863
See application file for complete search history.

(56) References Cited

U.S. PATENT DOCUMENTS

| | | |
|---|---|---|
| 544,021 A | 8/1895 | Chuntharapai et al. |
| 5,548,068 A | 8/1996 | Fischer et al. |
| 5,739,273 A | 4/1998 | Engelman et al. |
| 5,843,678 A | 12/1998 | Boyle |
| 6,124,429 A | 9/2000 | Miura et al. |
| 8,637,452 B2 | 1/2014 | Zhang et al. |
| 9,309,302 B2 | 4/2016 | Zhang et al. |
| 2002/0160416 A1 | 10/2002 | Boyle et al. |
| 2004/0215400 A1 | 10/2004 | Slovic et al. |
| 2010/0190188 A1 | 7/2010 | Henderson et al. |
| 2010/0249022 A1 | 9/2010 | Clapham et al. |
| 2011/0027910 A1 | 2/2011 | Weir et al. |
| 2011/0028700 A1 | 2/2011 | Heal |
| 2011/0046351 A1 | 2/2011 | Weir et al. |
| 2011/0112037 A1 | 5/2011 | Warne et al. |
| 2012/0165507 A1 | 6/2012 | Jazayeri-Dezfuly et al. |
| 2012/0252719 A1 | 10/2012 | Zhang et al. |
| 2013/0273585 A1 | 10/2013 | Appaiah et al. |
| 2014/0243277 A1 | 8/2014 | Zhang et al. |
| 2015/0370960 A1 | 12/2015 | Zhang et al. |
| 2015/0370961 A1 | 12/2015 | Zhang et al. |

FOREIGN PATENT DOCUMENTS

| | | | |
|---|---|---|---|
| EP | 1270724 A2 | 1/2003 | |
| WO | WO-2004/065363 A2 | 8/2004 | |
| WO | WO-2006/026355 A2 | 3/2006 | |
| WO | WO 2007/089899 | * 8/2007 | ........... C07K 14/705 |
| WO | WO-2007/089899 A2 | 8/2007 | |
| WO | WO-2007/141309 A2 | 12/2007 | |
| WO | WO-2008/114020 A2 | 9/2008 | |
| WO | WO 2008/143910 | * 11/2008 | ........... C07K 14/705 |
| WO | WO-2008/143910 A2 | 11/2008 | |
| WO | WO-2011/095625 A1 | 8/2011 | |
| WO | WO-2012/066330 A1 | 5/2012 | |
| WO | WO-2012/098413 A1 | 7/2012 | |
| WO | WO-2012/116203 A1 | 8/2012 | |
| WO | WO-2012/120315 A2 | 9/2012 | |
| WO | WO-2015/148820 A1 | 10/2015 | |

OTHER PUBLICATIONS

Slovic et al., PNAS (2004) 101(7), 1828-1833.*
Firestein, Nature (2001) 413, 211-218.*
Wienken et al., (Nature Communications (2010) 1(100), DOI: 10.1038/ncomms1093, 1-7.*
Betts and Russell, Chapter 14, Bioinformatics for Geneticists, ed. Barnes and Gray; (2003): John Wiley & Sons, p. 297.*
Database UniProt, RecName: Full-Olfactory Receptor, XP002733575, retrieved from EBI accession No. UNIPROT: B2N158, Jul. 2008.
Datta and Stone, "Soluble Mimics of a Chemokine Receptor: Chemokine Binding by Receptor Elements Juxtaposed on a Soluble Scaffold," *Protein Science*, 12:2482-2491 (2003).

(Continued)

*Primary Examiner* — Julie Ha
*Assistant Examiner* — Li N Komatsu
(74) *Attorney, Agent, or Firm* — McCarter & English, LLP; Thomas O. Hoover; Yu Lu

(57) ABSTRACT

The present invention is directed to a method of preparing a water-soluble variant of a G-protein coupled receptor (GPCR), the method comprising replacing residues leucine (L), isoleucine (I), valine (V), and phenylalanine (F) in hydrophilic surface α-helical positions b, c, and f but not positions a, d, e, and g within the 7-transmembrane α-helical domain of the GPCR with glutamine (Q), threonine (T), threonine (T), and tyrosine (Y), respectively.

15 Claims, 7 Drawing Sheets

(56) References Cited

OTHER PUBLICATIONS

Gene Infinity (pKa of amino acids chart, available at http://www.geneinfinity.org/sp/sp_aaprops.html).

Khafizov et al., "Ligand Specificity of Odorant Receptors," *J. Mol. Model*, 13:401-407 (2007).

Liang et al., "Computational studies 60-62, of membrane proteins: Models and predictions for biological understanding," *Biochimica et Biophysica Acta*,1818(4)927-941 (2012).

Ma et al., "NMR Studies of a Channel Protein without Membranes: Structure and Dynamics of Walter-Solubilized KcsA," *PNAS*, 105(43):16537-16542 (2008).

Marshall ("Amino Acid Chart," available at http://schools.nashua.edu/myclass/marshalii/anatomy/Pictures/FormsIDispForm.aspx?1 0=31, created Jan. 30, 2012, accessed on Feb. 17, 2015).

Park, "Structure of the Chemokine Receptor CXCR1 in Phospholipid Bilayers," *Nature*, 491:779-784 (2012).

Perez-Aguilar et al., "A Computationally Designed Water-Soluble Variant of a G-Protein-Coupled Receptor: The Human Mu Opioid Receptor," *PLOS One*, 8(6):e66009 (2013).

Slovic et al., "Computational Design of a Water-Soluble Analog of Phospholamban," *Protein Science*, 12:337-348 (2003).

Slovic et al., "Computational design of water-soluble analogues of the potassium channel KcsA," *Proc. Natl. Acad. Sci. U.S.*, 101 (7):1828-1833 (2004).

Slovic et al., "X-ray Structure of a Water-Soluble Analog of the Membrane Protein Phospholamban: Sequence Determinants Defining the Topology of Tetrameric and Pentameric Coiled Coils," *J. Mol. Biol.* 348:777-787 (2005).

Zhang et al. "Experimental and Computational Evaluation of Forces Directing the Association of Transmembrane Helices," *J. Am. Chem. Soc.*, 131:11341-11343 (2009).

Zhang et al., "The Mernbrane- and Soluble-Protein Helix-Helix Interactome: Similar Geometry via Different Interactions," *Structure*, 23:527-541 and Supplemental Information (2015).

Hesselgesser et al., Identification and characterization of the CXCR4 chemokine receptor in human T cell lines: ligand binding, biological activity, and HIV-1 infectivity. J Immunol. Jan. 15, 1998;160(2):877-83.

Liguo, Section 3 Amino Acid. Biochemistry. Beijing Normal University Publishing House. p. 6, Jun. 1988.

Liguo, Section 3 Amino Acid. Biochemistry. Beijing Normal University Publishing House. p. 6, Jun. 1988. Partial Translation Only.

Petsko, Protein Structure and Function. Science Press. pp. 14-15, Apr. 2009.

Petsko, Protein Structure and Function. Science Press. pp. 14-15, Apr. 2009. Partial Translation Only.

Youqi, How are proteins folded into a spherical structure. Chemistry of Life: Important Chemical Problems in Life Process. Hunan Science & Technology Press. Chapter 9, p. 43, Dec. 1998.

Youqi, How are proteins folded into a spherical structure. Chemistry of Life: Important Chemical Problems in Life Process. Hunan Science & Technology Press. Chapter 9, p. 43, Dec. 1998. Partial Translation Only.

\* cited by examiner

Design of a soluble 7-helical bundle of mOR103-15

SEQ ID NO: 2
SEQ ID NO: 1

```
                       Q    Q    Q Q   QT         QT  (8)
MERRNHTGRV SEFVLLGFPA PAPLRALLFF LSLLAYVLVL TENILIITAI
                     abcdefga   bcdefgabcd efgabcdefg Y          Y    T T   T    Q Y (7)
RNHPTLHKPM YFFLANMSFL EIWYVTVTIP KMLAGFIGSE ENHGQLISFE
a          a bcdefgabcd efgabcdefg abcdefg Q          T                T (3)       Q
ACMTQLYFFL GLGCTECVLL AVMAYDRYVA ICHPLHYPVI VSSRLCVQMA
abcdefgab  cdefgabcde fgabcdefga bc              abcdefg T   T  YQ (5)
AGSWAGGFGI SMVKVFLISR LSYCGPNTIN HFFCDVSPLL NLSCTDMSTA
abcdefgabc defgabcd
           Q Y T        T (4)
ELTDFILAIF ILLGPLSVTG ASYMAITGAV MRIPSAAGRH KAFSTCASHL
abcdefgab  cdefgabcde fgabcdefga          a bcdefgabcd T  TY      YT (5)                        T  Q     T Q (4)
TVVIIFYAAS IFIYARPKAL SAFDTNKLVS VLYAVIVPLL NPIIYCLRNQ
efgabcdefg abcd                 abcdef gabcdefgab cdefgabc EVKKALRRTL HLAQGQDANT KKSSRDGGSS GTETSQVAPA (36aa/340aa)
```

FIG. 1

WATER SOLUBLE MEMBRANE PROTEINS AND METHODS FOR THE PREPARATION AND USE THEREOF

RELATED APPLICATIONS

This application is a continuation of U.S. application Ser. No. 14/105,252, filed Dec. 13, 2013, now U.S. Pat. No. 9,309,302; which is a continuation of U.S. application Ser. No. 13/403,725, filed Feb. 23, 2012, now U.S. Pat. No. 8,637,452; which claims the benefit of U.S. Provisional Application No. 61/445,740, filed on Feb. 23, 2011. The entire teachings of each of the above applications are incorporated herein by reference in their entirety.

BACKGROUND OF THE INVENTION

Membrane proteins play vital roles in all living systems. Approximately ~30% of all genes in almost all sequenced genomes, code for membrane proteins. However, our detailed understanding of their structure and function lags far behind that of soluble proteins. As of February 2012, there are over 79,500 structures in the Protein Data Bank, however, there are 952 membrane protein structures with 320 unique structures including 8 G-protein coupled receptors. Although there are about 400 functional olfactory receptors in human, not a single olfactory receptor has been determined.

There are several bottlenecks in elucidating the structure and function of olfactory receptors and their recognition and odorant-binding properties although they are of great interest. The most critical and challenging task is that it is extremely difficult to produce milligrams quantities of soluble and stable receptors. Inexpensive large-scale production methods are desperately needed, and have thus been the focus of extensive research. It is only possible to conduct detailed structural studies once these preliminary obstacles have been surmounted. Therefore, there is a need in the art for improved methods of studying G-protein coupled receptors, including olfactory receptors.

SUMMARY OF THE INVENTION

The present invention is directed to water-soluble membrane peptides, compositions comprising said peptides, methods for the preparation thereof and methods of use thereof.

The invention encompasses a water-soluble polypeptide comprising a modified α-helical domain, wherein the modified α-helical domain comprises an amino acid sequence in which one or more hydrophobic amino acid residues within a α-helical domain of a native membrane protein is replaced with one or more hydrophilic amino acid residues. The invention also encompasses a method of preparing a water-soluble polypeptide comprising replacing one or more hydrophobic amino acid residues within the α-helical domain of a native membrane protein with one or more hydrophilic amino acid residues. The invention additionally encompasses a polypeptide prepared by replacing one or more hydrophobic amino acid residues within the α-helical domain of a native membrane protein with one or more hydrophilic amino acid residues.

The invention further encompasses a method of treatment for a disorder or disease that is mediated by the activity a membrane protein in a subject in need thereof, comprising administering to said subject an effective amount of a water-soluble polypeptide comprising a modified α-helical domain, wherein the modified α-helical domain comprises an amino acid sequence in which one or more hydrophobic amino acid residues within a α-helical domain of the membrane protein is replaced with one or more hydrophilic amino acid residues.

In certain aspects, the water-soluble polypeptide retains the ligand-binding activity of the membrane protein. Examples of disorders and diseases that can be treated by administering a water-soluble peptide of the invention include, but are not limited to, cancer (such as, small cell lung cancer, melanoma, triple negative breast cancer), Parkinson's disease, cardiovascular disease, hypertension, and bronchial asthma.

The invention also encompasses a pharmaceutical composition comprising a water-soluble polypeptide of the invention and pharmaceutically acceptable carrier or diluent.

In some aspects, the α-helical domain is a 7-transmembrane α-helical domain. In an additional embodiment, the native membrane protein is a G-protein coupled receptor (GPCR). In some aspects of this embodiment, the GPCR is selected from the group comprising purinergic receptors ($P2Y_1$, $P2Y_2$, $P2Y_4$, $P2Y_6$), $M_1$ and $M_3$ muscarinic acetylcholine receptors, receptors for thrombin [protease-activated receptor (PAR)-1, PAR-2], thromboxane ($TXA_2$), sphingosine 1-phosphate ($S1P_2$, $S1P_3$, $S1P_4$ and $S1P_5$), lysophosphatidic acid ($LPA_1$, $LPA_2$, $LPA_3$), angiotensin II ($AT_1$), serotonin (5-$HT_2$, and 5-$HT_4$), somatostatin ($sst_5$), endothelin ($ET_A$ and $ET_B$), cholecystokinin ($CCK_1$), $V_{1a}$ vasopressin receptors, $D_5$ dopamine receptors, fMLP formyl peptide receptors, $GAL_2$ galanin receptors, $EP_3$ prostanoid receptors, $A_1$ adenosine receptors, $\alpha_1$ adrenergic receptors, $BB_2$ bombesin receptors, $B_2$ bradykinin receptors, calcium-sensing receptors, chemokine receptors, KSHV-ORF74 chemokine receptors, $NK_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4. In yet an additional embodiment, the native membrane protein or membrane protein is an integral membrane protein. In a further aspect, the native membrane protein is a mammalian protein. In yet a further aspect, the native membrane protein is an olfactory receptor. In additional embodiments, the olfactory receptor is mOR103-15.

In some aspects, the hydrophilic residues (which replace one or more hydrophobic residues in the α-helical domain of a native membrane protein) are selected from the group consisting of glutamine (Q), threonine (T), tyrosine (Y) and any combination thereof. In additional aspects, one or more hydrophobic residues selected from leucine (L), isoleucine (I), valine (V) and phenylalanine (F) are replaced.

In certain embodiments, one or more phenylalanine residues of the α-helical domain of the protein are replaced with tyrosine. In certain additional embodiments, one or more isoleucine and/or valine residues of the α-helical domain of the protein are replaced with threonine. In yet additional aspects, one or more phenylalanine residues of the α-helical domain of the protein are replaced with tyrosine and one or more isoleucine and/or valine residues of the α-helical domain of the protein are replaced with threonine. In additional embodiments, one or more leucine residues of the α-helical domain of the protein are replaced with glutamine. In yet additional embodiments, one or more leucine residues of the α-helical domain of the protein are replaced with glutamine and one or more isoleucine and/or valine residues of the protein are replaced with threonine. In further embodiments, one or more leucine residues of the α-helical domain of the protein are replaced with glutamine and one or more phenylalanine residues of the α-helical domain of the protein are replaced with tyrosine. In yet additional aspects, one or more leucine residues of the α-helical domain of the protein are replaced with glutamine, one or more phenylalanine residues of the α-helical domain of the protein are replaced with tyrosine, and one or more isoleucine and/or valine residues of the α-helical domain of the protein are replaced with threonine.

In additional embodiments, the water-soluble polypeptide retains at least some of the biological activity of the native membrane protein. In an aspect of this embodiment, the water-soluble polypeptide retains the ability to bind the ligand which normally binds to the native membrane protein. In another embodiment, one or more amino acids within potential ligand binding sites of the native membrane protein are not replaced. In an aspect of this embodiment, examples of native membrane proteins with one or more amino acids not replaced within potential ligand-binding sites are purinergic receptors (P2Y$_1$, P2Y$_2$, P2Y$_4$, P2Y$_6$), M$_1$ and M$_3$ muscarinic acetylcholine receptors, receptors for thrombin [protease-activated receptor (PAR)-1, PAR-2], thromboxane (TXA$_2$), sphingosine 1-phosphate (S1P$_2$, S1P$_3$, S1P$_4$ and S1P$_5$), lysophosphatidic acid (LPA$_1$, LPA$_2$, LPA$_3$), angiotensin II (AT$_1$), serotonin (5-HT$_{2c}$ and 5-HT$_4$), somatostatin (sst$_5$), endothelin (ET$_A$ and ET$_B$), cholecystokinin (CCK$_1$), V$_{1a}$ vasopressin receptors, D$_5$ dopamine receptors, fMLP formyl peptide receptors, GAL$_2$ galanin receptors, EP$_3$ prostanoid receptors, A$_1$ adenosine receptors, α$_1$ adrenergic receptors, BB$_2$ bombesin receptors, B$_2$ bradykinin receptors, calcium-sensing receptors, chemokine receptors, KSHV-ORF74 chemokine receptors, NK$_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4.

In another embodiment, one or more amino acids within potential odorant binding sites of the native membrane protein are not replaced.

In one embodiment, water-soluble polypeptide comprising a modified α-helical domain comprises the amino acid sequence of MERRNHTGRV SEFVLLGFPA PAPQRALQFF QSLQAYVQTL TENIQTITAI RNHPTLH-KPM YYFLANMSFYL ETWYTTVTTP KMQAGYIGSE ENHGQLISFE ACMTQLYFFQ GLGCTECTLL AVMAY-DRYVA TCHPLHYPVI VSSRQCVQMA AGSWAGGFGT SMTVKVYQISR LSYCGPNTIN HFFCDVSPLL NLSCT-DMSTA ELTDFILAIF ILLGPLSVTG ASYMAITGAV MRIPSAAGRH KAFSTCASHL TTVITYYAAS IYTYAR-PKAL SAFDTNKLVS VLYAVIVPLL NPIIYCLRNQ EVKKALRRTL HLAQGDANT KKSSRDGGSS GTETSQVAPA (SEQ ID NO: 2). In yet an additional embodiment, the water-soluble polypeptide comprising a modified 7-transmembrane α-helical domain comprises one or more of the following amino acid sequences:

|   |   | (SEQ ID NO: 3) |
|---|---|---|
| a. | PQRALQFFQSLQAYVQTLTENIQTITAI R | |

|   |   | (SEQ ID NO: 4) |
|---|---|---|
| b. | MYYFLANMSFYLETWYTTVTTPKMQAGYI | |

|   |   | (SEQ ID NO: 5) |
|---|---|---|
| c. | CMTQLYFFQGLGCTECTLLAVMAYDRYVA TC | |

|   |   | (SEQ ID NO: 6) |
|---|---|---|
| d. | RQCVQMAAGSWAGGFGTSMTVKVYQ | |

|   |   | (SEQ ID NO: 7) |
|---|---|---|
| e. | LTDFILAIFILLGPLSVTGASYMAITGAV | |

|   |   | (SEQ ID NO: 8) |
|---|---|---|
| f. | HKAFSTCASHLTTVITYYAAS IYTY | |

|   |   | (SEQ ID NO: 9) |
|---|---|---|
| g. | TNKLVSVLYAVIVPLLNPIIYCLRN | |

In certain aspects of the invention, the secondary structure of the water-soluble peptide is determined. In some embodiments, the secondary structure is determined using circular dichroism.

In certain embodiments, ligand binding to the water-soluble polypeptide is measured. In some aspects, ligand binding affinity of the water-soluble polypeptide is compared to that of the native protein. In additional aspects, ligand binding is measured using microscale thermophoresis, calcium influx assay or any combination thereof.

In yet an additional embodiment, the invention encompasses a cell transfected with a water-soluble peptide comprising a modified α-helical domain. In certain embodiments, the cell is a mammalian cell. One example of a mammalian cell that can be transfected is a HEK293 cell.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows the amino acid sequences of native mOR103-15 and mutated mOR103-15 using glutamine, threonine and tyrosine (QTY) replacements. Use of QTY replacements to systematically mutate key residues on the 7-transmembrane α-helices to convert a water-insoluble olfactory receptor into a water-soluble one. We only change the positions of b, c, f with the more water-soluble residues Q, T, Y. These positions are on the hydrophilic face of the helices. We maintain the positions a, d, e, g that are on the hydrophobic face. It is likely that these changes will maintain the individual α-helices. The mutations are labeled in capital letters on top of the receptor sequence. The small letters, abcdefg, are helical wheel positions. The underlines are the locations of 7-transmembrane α-helices. The numbers (8, 7, 3, 5, 4, 5, 4) are mutations in each α-helix. There are 36-residue changes, ~10.5% of the total 340 residues.

FIG. 3A is the top view of the QTY replacements. FIG. 3B is the side view of the QTY replacements. Note the mutations are only on one side of the helices. The native receptor without mutations has a folded structure similar to α$_1$ adrenergic receptor, whereas after mutation, the structure is similar to the β2 adrenergic receptor. FIG. 3C shows the simulated structures of superimposed native mOR103-15 and designed QTY mutation of mOR103-15. The overall structural difference is ~0.8 Å average.

In FIG. 6A, we have changed positions b, c, f with the more water-soluble residues Q, T, Y. We do not change the positions a, d, e, g. These positions are believed to maintain the specific clustering of individual alpha-helices. FIG. 6B shows the superimpositions of membrane form CXCR4 and QTY water-soluble CXCR4. In FIG. 6C, the native residues are labeled in dark letters and in FIG. 6D, mutations are labeled in darker letters in the sequence. A total of 29 QTY mutations among 352 residues have been made (about 8.2%) in the seven transmembrane helical segments. These mutations do not change the charged residues, so the variant receptor mass and pI remain largely unchanged. The molecular shapes and sizes of amino acids, Q, T and Y are very similar to L, V/I and Y, so there are minimal overall, local shape changes.

DETAILED DESCRIPTION OF THE INVENTION

A description of preferred embodiments of the invention follows.

The words "a" or "an" are meant to encompass one or more, unless otherwise specified.

In some aspects, the invention is directed to the use of the QTY (Glutamine, threonine and tyrosine) replacement method to systematically change the 7-transmembrane α-helix hydrophobic residues leucine (L), isoleucine (I), valine (V), and phenylalanine (F) of a native protein to the hydrophilic residues glutamine (Q), threonine (T) and tyrosine (Y). This invention will convert the native membrane protein from a water-insoluble one to a water-soluble counterpart.

Another innovation of the invention is to convert the water-insoluble olfactory receptor mOR103-15 into a water-soluble one with about 10.5% specific residues changes (36aa/340aa). This will be accomplished by systematically and selectively changing key residues at the α-helical positions b, c, f that usually face the hydrophilic surface, while maintaining the hydrophobic residues at α-helical positions a, d, e, g. The synthetic biology design method is general and broadly applicable to the study of other olfactory receptors and G-protein coupled receptors. This strategy has the potential to overcome the bottleneck of crystallizing olfactory receptors, as well as additional GPCRs and other membrane proteins.

Figure 2:
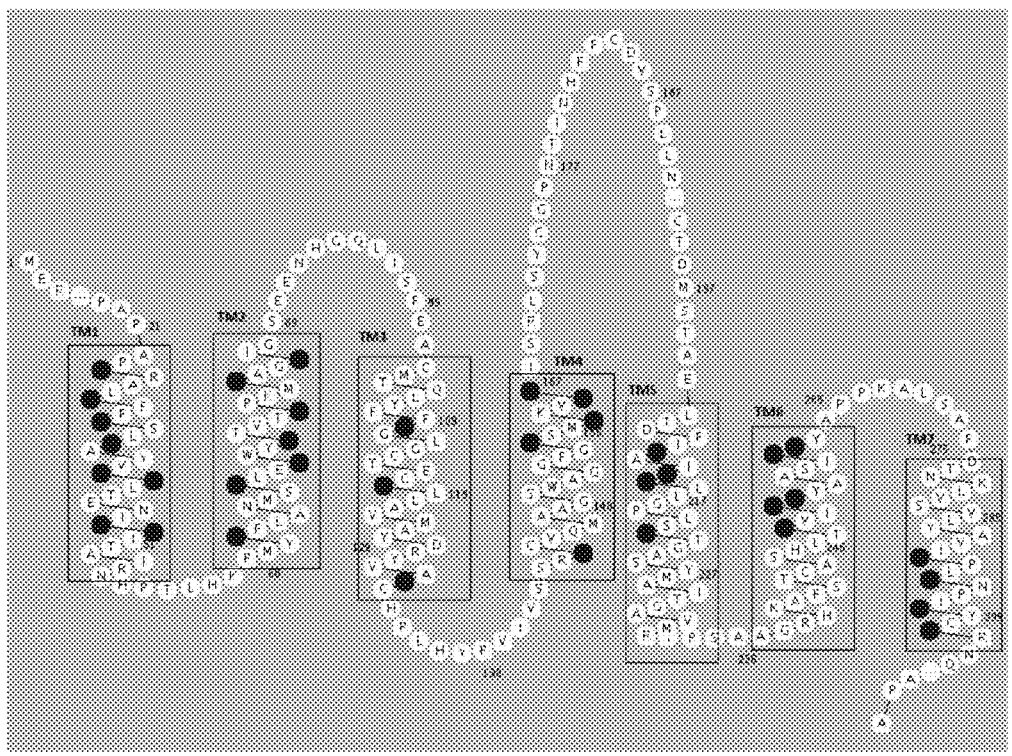
FIG. 2 shows molecular models of a QTY Replacement olfactory receptor mOR103-15. A total 36 mutations have been made (~10.5%) in the 7-transmembrane helical segments. These mutations do not change the charged residues, so the variant receptor mass and pI remain largely unchanged. The molecular shapes and sizes of amino acids, Q, T, and Y are very similar to L, V/I and Y, so there are minimal overall local shape changes. A segment of 20 amino acids at the C-terminus are not modeled for clarity.

We used synthetic biology methods to convert a water-insoluble olfactory receptor into a water-soluble one with ~10.5% of the residues changes (36aa/340aa) (FIGS. 1 and 2). We have systematically and selectively changed key residues at the α-helical positions b, c, f (which usually form the hydrophilic surface), but maintained the hydrophobic residues at α-helical positions a, d, e, g (FIG. 1). Our synthetic biology design method is general in nature, thus it is broadly applicable to the study other olfactory receptors, chemokine CXCR4 as well as other G-protein coupled receptors (GPCRs) and other membrane proteins. This simple strategy may partly overcome the bottleneck of structural studies of olfactory receptors, GPCRs, and other membrane proteins if the converted water-soluble membrane proteins remain biologically functional.

Figure 3A:
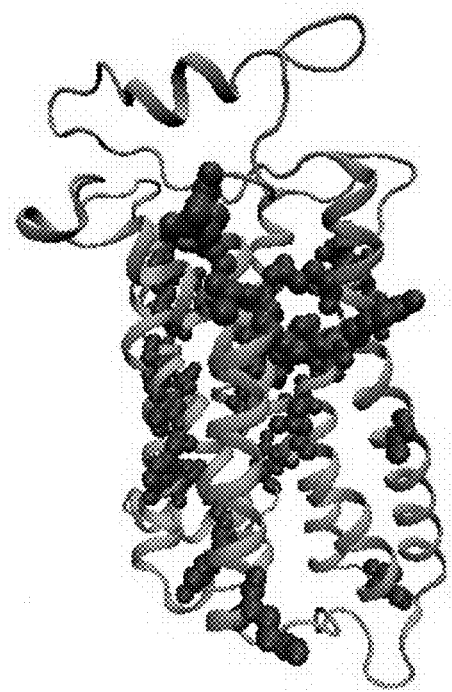
FIGS. 3A-3C.
Figure 3B:
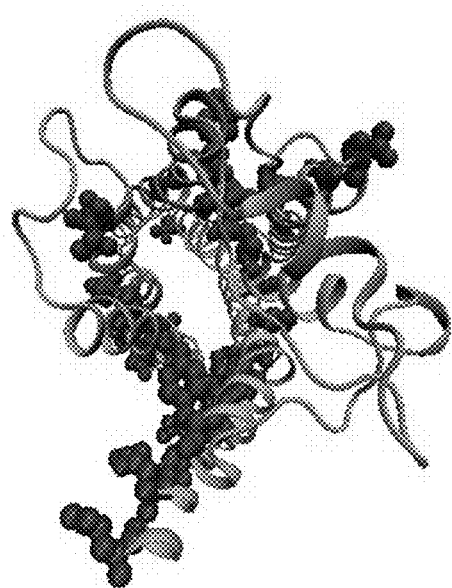
Figure 3C:
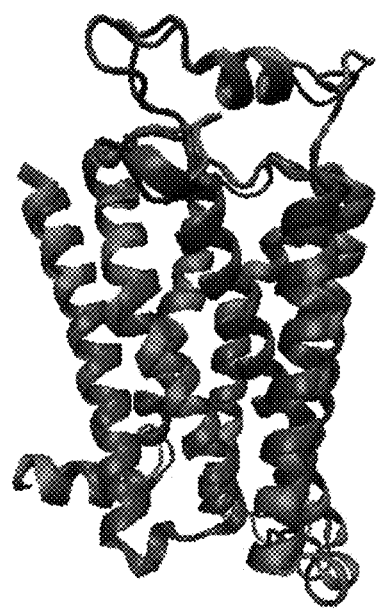

In order to facilitate the study of the structural aspects of olfactory receptors and their binding properties, we will use the QTY replacement method to design a water-soluble 7-bundle helical olfactory receptor mOR103-15 (FIGS. 1-3). It is known that seven amino acids have α-helical forming tendencies (32): leucine (L) (1.30), glutamine (Q) (1.27), phenylalanine (F) (1.07), tyrosine (Y) (0.72), isoleucine (I) (0.97), valine (V) (0.91) and threonine (T) (0.82). We also know that side chains of Q, Y and T can all form hydrogen bonds with water: Q can form 4 H-bonds (2 H-donors from —NH$_2$, 2 H-acceptors from C=O), and T and Y can form 3 H-bonds each (—OH, 1-H donor from —H and 2 acceptors from —O). The Q, T, Y residues are more water-soluble than L, F, I, or V, which cannot form any hydrogen bonds with their side chains. The proposed substitutions will not have any positive- or negative-charges changes. Furthermore, the molecular shapes and sizes are very similar for the pairs: leucine/glutamine, phenylalanine/tyrosine, valine/threonine, and isoleucine/threonine (33-34). The proposed changes should thus increase the solubility of 7-transmembrane α-helices while maintaining the overall helical structure (FIG. 3C).

In this soluble olfactory receptor design, we have performed the following substitutions: phenylalanine to tyrosine (F→Y), isoleucine/valine to threonine (I/V→T), and leucine to glutamine (L→Q). The secondary structure of the water-soluble olfactory receptor, as well as measure its odorant-binding capabilities can be examined. If odorant-binding is detected with the QTY replacements, then it is likely that we have preserved important components of the original structure. The secondary structure and binding of the designed water-soluble olfactory receptor with the native olfactory receptor can be prepared. Milligram quantities of the water-soluble receptor can be produced and crystal screens can be set up with and without odorants.

In one embodiment, the native membrane protein is a G-protein coupled receptor (GPCR). In yet another embodiment, the native membrane protein is an olfactory receptor. In some embodiments, the olfactory receptor is a mammalian receptor. In yet another embodiment, the olfactory receptor is mOR103-15. In certain aspects, the water-soluble polypeptide retains at least some of the biological activity of the native membrane protein. In yet another aspect, the membrane protein is a membrane receptor that mediates a disease or condition.

In a further embodiment, the native membrane protein is a GPCR selected from the group comprising purinergic receptors (P2Y$_1$, P2Y$_2$, P2Y$_4$, P2Y$_6$), M$_1$ and M$_3$ muscarinic acetylcholine receptors, receptors for thrombin [protease-activated receptor (PAR)-1, PAR-2], thromboxane (TXA$_2$), sphingosine 1-phosphate (S1P$_2$, S1P$_3$, S1P$_4$ and S1P$_5$), lysophosphatidic acid (LPA$_1$, LPA$_2$, LPA$_3$), angiotensin II (AT$_1$), serotonin (5-HT$_{2c}$ and 5-HT$_4$), somatostatin (sst$_5$), endothelin (ET$_A$ and ET$_B$), cholecystokinin (CCK$_1$), V$_{1a}$ vasopressin receptors, D$_5$ dopamine receptors, fMLP formyl peptide receptors, GAL$_2$ galanin receptors, EP$_3$ prostanoid receptors, A$_1$ adenosine receptors, α$_1$ adrenergic receptors, BB$_2$ bombesin receptors, B$_2$ bradykinin receptors, calcium-sensing receptors, chemokine receptors, KSHV-ORF74 chemokine receptors, NK$_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4. In a further embodiment, the invention is directed to a pharmaceutical composition or method of treatment described herein wherein the native membrane protein is a GPCR selected from the group comprising purinergic receptors (P2Y$_1$, P2Y$_2$, P2Y$_4$, P2Y$_6$), M$_1$ and M$_3$ muscarinic acetylcholine receptors, receptors for thrombin [protease-activated receptor (PAR)-1, PAR-2], thromboxane (TXA$_2$), sphingosine 1-phosphate (S1P$_2$, S1P$_3$, S1P$_4$ and S1P$_5$), lysophosphatidic acid (LPA$_1$, LPA$_2$, LPA$_3$), angiotensin II (AT$_1$), serotonin (5-HT$_2$, and 5-HT$_4$), somatostatin (sst$_5$), endothelin (ET$_A$ and ET$_B$), cholecystokinin (CCK$_1$), V$_{1a}$ vasopressin receptors, D$_5$ dopamine receptors, fMLP formyl peptide receptors, GAL$_2$ galanin receptors, EP$_3$ prostanoid receptors, A$_1$ adenosine receptors, α$_1$ adrenergic receptors, BB$_2$ bombesin receptors, B$_2$ bradykinin receptors, calcium-sensing receptors, chemokine receptors, KSHV-ORF74 chemokine receptors, NK$_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4.

In another embodiment, the water-soluble polypeptide retains the at least some of the ligand-binding activity of the membrane protein. In some embodiments, the GPCRs are mammalian receptors.

In a further embodiment, one or more amino acids within potential ligand binding sites of the native membrane protein are not replaced. In an aspect of this embodiment, examples of native membrane proteins with potential ligand-binding sites having one or more amino acids not replaced include purinergic receptors (P2Y$_1$, P2Y$_2$, P2Y$_4$, P2Y$_6$), M$_1$ and M$_3$ muscarinic acetylcholine receptors, receptors for thrombin [protease-activated receptor (PAR)-1, PAR-2], thromboxane (TXA$_2$), sphingosine 1-phosphate (S1P$_2$, S1P$_3$, S1P$_4$ and S1P$_5$), lysophosphatidic acid (LPA$_1$, LPA$_2$, LPA$_3$), angiotensin II (AT$_1$), serotonin (5-HT$_2$, and 5-HT$_4$), somatostatin (sst$_5$), endothelin (ET$_A$ and ET$_B$), cholecystokinin (CCK$_1$), V$_{1a}$ vasopressin receptors, D$_5$ dopamine receptors, fMLP formyl peptide receptors, GAL$_2$ galanin receptors, EP$_3$ prostanoid receptors, A$_1$ adenosine receptors, α$_1$ adrenergic receptors, BB$_2$ bombesin receptors, B$_2$ bradykinin receptors, calcium-sensing receptors, chemokine receptors, KSHV-ORF74 chemokine receptors, NK$_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4.

The invention further encompasses a method of treatment for a disorder or disease that is mediated by the activity of a membrane protein, comprising the use of a water-soluble polypeptide to treat said disorders and diseases, wherein said water-soluble polypeptide comprises a modified α-helical domain, and wherein said water-soluble polypeptide retains the ligand-binding activity of the native membrane protein. Examples of such disorders and diseases include, but are not limited to, cancer, small cell lung cancer, melanoma, breast cancer, Parkinson's disease, cardiovascular disease, hypertension, and asthma.

As described herein, the water-soluble peptides described herein can be used for the treatment of conditions or diseases mediated by the activity of a membrane protein. In certain aspects, the water-soluble peptides can act as "decoys" for the membrane receptor and bind to the ligand that activates the membrane receptor. As such, the water-soluble peptides described herein can be used to reduce the activity of a membrane protein. These water-soluble peptides can remain in the circulation and bind to specific ligands, thereby reducing the activity of membrane bound receptors. For example, the GPCR CXCR4 is over-expressed in small cell lung cancer and facilitates metastasis of tumor cells. Binding of this ligand by a water-soluble peptide such as that described herein may significantly reduce metastasis.

The chemokine receptor, CXCR4, is known in viral research as a major coreceptor for the entry of T cell line-tropic HIV (Feng, et al. (1996) *Science* 272: 872-877; Davis, et al. (1997) *J Exp Med* 186: 1793-1798; Zaitseva, et al. (1997) Nat Med 3: 1369-1375; Sanchez, et al. (1997) *J Biol Chem* 272: 27529-27531). T Stromal cell derived factor 1 (SDF-1) is a chemokine that interacts specifically with CXCR4. When SDF-1 binds to CXCR4, CXCR4 activates Gαi protein-mediated signaling (pertussis toxin-sensitive) (Chen, et al. (1998) *Mol Pharmacol* 53: 177-181), including downstream kinase pathways such as Ras/MAP Kinases and phosphatidylinositol 3-kinase (PI3K)/Akt in lymphocyte, megakaryocytes, and hematopoietic stem cells (Bleul, et al. (1996) *Nature* 382: 829-833; Deng, et al. (1997) *Nature* 388: 296-300; Kijowski, et al. (2001) *Stem Cells* 19: 453-466; Majka, et al. (2001) *Folia. Histochem. Cytobiol.* 39: 235-244; Sotsios, et al. (1999) *J. Immunol.* 163: 5954-5963; Vlahakis, et al. (2002) *J. Immunol.* 169: 5546-5554). In mice transplanted with human lymph nodes, SDF-1 induces CXCR4-positive cell migration into the transplanted lymph node (Blades, et al. (2002) *J. Immunol.* 168: 4308-4317).

Recently, studies have shown that CXCR4 interactions may regulate the migration of metastatic cells. Hypoxia, a reduction in partial oxygen pressure, is a microenvironmental change that occurs in most solid tumors and is a major inducer of tumor angiogenesis and therapeutic resistance. Hypoxia increases CXCR4 levels (Staller, et al. (2003) *Nature* 425: 307-311). Microarray analysis on a sub-population of cells from a bone metastatic model with elevated metastatic activity showed that one of the genes increased in the metastatic phenotype was CXCR4. Furthermore, over-expression CXCR4 in isolated cells significantly increased the metastatic activity (Kang, et al. (2003) *Cancer Cell* 3: 537-549). In samples collected from various breast cancer patients, Muller et al. (Muller, et al. (2001) *Nature* 410: 50-56) found that CXCR4 expression level is higher in primary tumors relative to normal mammary gland or epithelial cells. Moreover, CXCR4 antibody treatment has been shown to inhibit metastasis to regional lymph nodes when compared to control isotypes that all metastasized to lymph nodes and lungs (Muller, et al. (2001)). As such a decoy therapy model is suitable for treating CXCR4 mediated diseases and disorders.

In another embodiment of the invention relates to the treatment of a disease or disorder involving CXCR4-dependent chemotaxis, wherein the disease is associated with aberrant leukocyte recruitment or activation. The disease is selected from the group consisting of arthritis, psoriasis, multiple sclerosis, ulcerative colitis, Crohn's disease, allergy, asthma, AIDS associated encephalitis, AIDS related maculopapular skin eruption, AIDS related interstitial pneumonia, AIDS related enteropathy, AIDS related periportal hepatic inflammation and AIDS related glomerulo nephritis.

In another aspect, the invention relates to the treatment of a disease or disorder selected from arthritis, lymphoma, non-small lung cancer, lung cancer, breast cancer, prostate cancer, multiple sclerosis, central nervous system developmental disease, dementia, Parkinson's disease, Alzheimer's disease, tumor, fibroma, astrocytoma, myeloma, glioblastoma, an inflammatory disease, an organ transplantation rejection, AIDS, HIV-infection or angiogenesis.

The invention also encompasses a pharmaceutical composition comprising said water-soluble polypeptide and a pharmaceutically acceptable carrier or diluent.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The compositions and pharmacologic agents described herein can be administered in the form of a depot injection or implant preparation which can be formulated in such a manner as to permit a sustained or pulsatile release of the active ingredient.

Transdermal administration includes percutaneous absorption of the composition through the skin. Transdermal formulations include patches, ointments, creams, gels, salves and the like. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

"Treating" or "treatment" includes preventing or delaying the onset of the symptoms, complications, or biochemical indicia of a disease, alleviating or ameliorating the symptoms or arresting or inhibiting further development of the disease, condition, or disorder. A "patient" is a human subject in need of treatment.

An "effective amount" refers to that amount of the therapeutic agent that is sufficient to ameliorate of one or more symptoms of a disorder and/or prevent advancement of a disorder, cause regression of the disorder and/or to achieve a desired effect.

The invention will be better understood in connection with the following example, which is intended as an illustration only and not limiting of the scope of the invention. Various changes and modifications to the disclosed embodiments will be apparent to those skilled in the art and such changes and may be made without departing from the spirit of the invention and the scope of the appended claims.

EXAMPLES

Example 1: Systematic Analyses of the Ligand-Binding Properties of Factory Receptors The Q (Glutamine) T (Threonine) Y (Tyrosine) QTY replacement are used to convert a water-insoluble olfactory receptor to a water-soluble one for biochemical, biophysical and structural analyses. Our specific aims are to:

1) Use the QTY (Glutamine, threonine and tyrosine) replacement method to systematically change the 7-transmembrane α-helix hydrophobic residues leucine (L), isoleucine (I), valine (V), and phenylalanine (F) to the hydrophilic residues glutamine (Q), threonine (T) and tyrosine (Y). This method converts the protein from a water-insoluble olfactory receptor to a water-soluble one.

2) Produce and purify milligram quantities of native and bioengineered olfactory receptors using commercial cell-free in vitro translation systems (Invitrogen and Qiagen).

3) Determine the secondary structure of the purified olfactory receptors using circular dichroism (CD).

4) Determine the binding affinity of the native and bioengineered olfactory receptor variants using microscale thermophoresis.

5) Transfect the native and variant OR genes into HEK293 cells, and use calcium influx assays to measure odorant activation of the native and mutant olfactory receptors. These measurements will correlate the microscale thermophoresis binding data to functional responses within cells.

6) Systematically screen the native and bioengineered olfactory receptors for crystallizing conditions in the presence and absence of odorants and the presence and absence of detergent.

Research Strategy

Use QTY replacement to design a soluble 7-helical bundle olfactory receptor mOR103-15. An innovation of our study is to convert the water-insoluble olfactory receptor mORI03-15 into a water soluble one with about 10.5% specific residues changes (36aa/340aa). We have systematically and selectively changed key residues at the α-helical positions b, c, f that usually face the hydrophilic surface, while maintaining the hydrophobic residues at α-helical positions a, d, e, g. Our synthetic biology design method is general and broadly applicable to the study of other olfactory receptors and G-protein coupled receptors. This strategy has the potential to overcome the bottleneck of crystallizing olfactory receptors, as well as additional GPCRs and other membrane proteins. While our design to change the solubility of the sequence is focused on the b,c,f positions of the helical wheel, some further changes to other parts of the sequence can be made without significantly affecting the function or structure of the peptide, polypeptide or protein. For example conservative mutations can be made.

The Experimental Approach

1) Use of QTY replacements to design a water-soluble 7-helical bundle olfactory receptor mOR103-15. We used (L→Q), isoleucine/valine→threonine (IN→T) and phenylalanine→tyrosine (F→Y). In the study, we can examine the secondary structure of the water-soluble olfactory receptor, as well as measure its odorant-binding capabilities. If odorant-binding is measured with the QTY replacements, then it is likely that we have preserved important components of the original structure. We can compare the secondary structure and binding of native olfactory receptor with the designed water-soluble olfactory receptor. We can also produce milligram quantities of the water-soluble receptor, and set up crystal screens with and without odorants.

```
MERRNHTGRV  SEFVLLGFPA  PAPQRALQFF  QSLQAYVQTL  TENIQTITAI  RNHPTLHKPM  YYFLANMSYL  ETWYTTVTTP
                        abcdefga    bcdefgabcd  efgabcdefg  a           a bcdefgabcd efgabcdefg KMQAGYIGSE  ENHGQLISFE  ACMTQLYFFQ  GLGCTECTLL  AVMAYDRYVA  TCHPLHYPVI  VESRQCVQMA  AGSWAGGFGT
abcdefg                 abcdefgab   cdefgabcde  fgabcdefga  bc                abcdefg abcdefgabc SMTKVYQISR  LSYCGPNTIN  HFFCDVSPLL  NLSCTDMSTA  ELTDFIQAIY  TLLGPLSTTG  ASYMAITGAV  MRIPSAAGRH
defgabcd                                        abcdefgab   cdefgabcde  fgabcdefga           a KAFSTCASHL  TTVITYYAAS  IYTYARPKAL  SAFDTNKLVS  VLYAVITPLQ  NPITYCQRNQ  EVKKALRRTL  HLAQGQDANT
bcdefgabcd  efgabcdefg  abcd                    abcdef      gabcdefgab  cdefgabc KKSSRDGGSS  GTETSQVAPA.  (36aa mutations/340aa, ~10.5% mutations)
``` synthetic biology methods to convert a water-insoluble olfactory receptor into a water-soluble one with ~10.5% of the residues changes (36aa/340aa) (FIGS. 1-3). We have systematically and selectively changed key residues at the α-helical positions b, c, f (which usually form the hydrophilic surface), but maintained the hydrophobic residues at α-helical positions a, d, e, g (FIG. 1). Our synthetic biology design method is general in nature, thus it is broadly applicable to the study other olfactory receptors as well as other G-protein coupled receptors (GPCRs). This simple strategy may partly overcome the bottleneck of structural studies of olfactory receptors, GPCRs, and other membrane proteins if the converted water-soluble membrane proteins remain biologically functional.

In order to facilitate the study of the structural aspects of olfactory receptors and their binding properties, we can use the QTY replacement method to design a water-soluble 7-bundle helical olfactory receptor mORI03-15 (FIGS. 1-3). It is known that seven amino acids have α-helical forming tendencies (32): leucine (L) (1.30), glutamine (Q) (1.27), phenylalanine (F) (1.07), tyrosine (Y) (0.72), isoleucine (I) (0.97), valine (V) (0.91) and threonine (T) (0.82). We also know that side chains of Q, Y and T can all form hydrogen bonds with water: Q can form 4 H-bonds (2 H-donors from —NH$_2$, 2 H-acceptors from C=O), and T and Y can form 3 H-bonds each (—OH, I—H donor from —H and 2 acceptors from —O). The Q, T, Y residues are more water-soluble than L, F, I, or V, which cannot form any hydrogen bonds with their side chains. The substitutions will not have any positive- or negative-charges changes. Furthermore, the molecular shapes and sizes are very similar for the pairs: leucine/glutamine, phenylalaine/tyrosine, valine/threonine, and isoleucine/threonine. The changes increase the solubility of 7-transmembrane α-helices while maintaining the overall helical structure.

In this soluble olfactory receptor design, we have performed the following substitutions: leucine→glutamine 2) Produce and purify milligram quantities of native and bioengineered variants of olfactory receptors. We can use commercial cell-free systems to produce milligrams of native and water-soluble mOR103-15. We can use the optimized protocols we have developed in our lab: this is the key advancement and innovation we have accomplished in the last few years. We can produce and purify the native and variant olfactory receptors in one day using immunoaffinity purification. Gel filtration can then be used to separate the monomeric and dimeric receptor forms.

Figure 4:
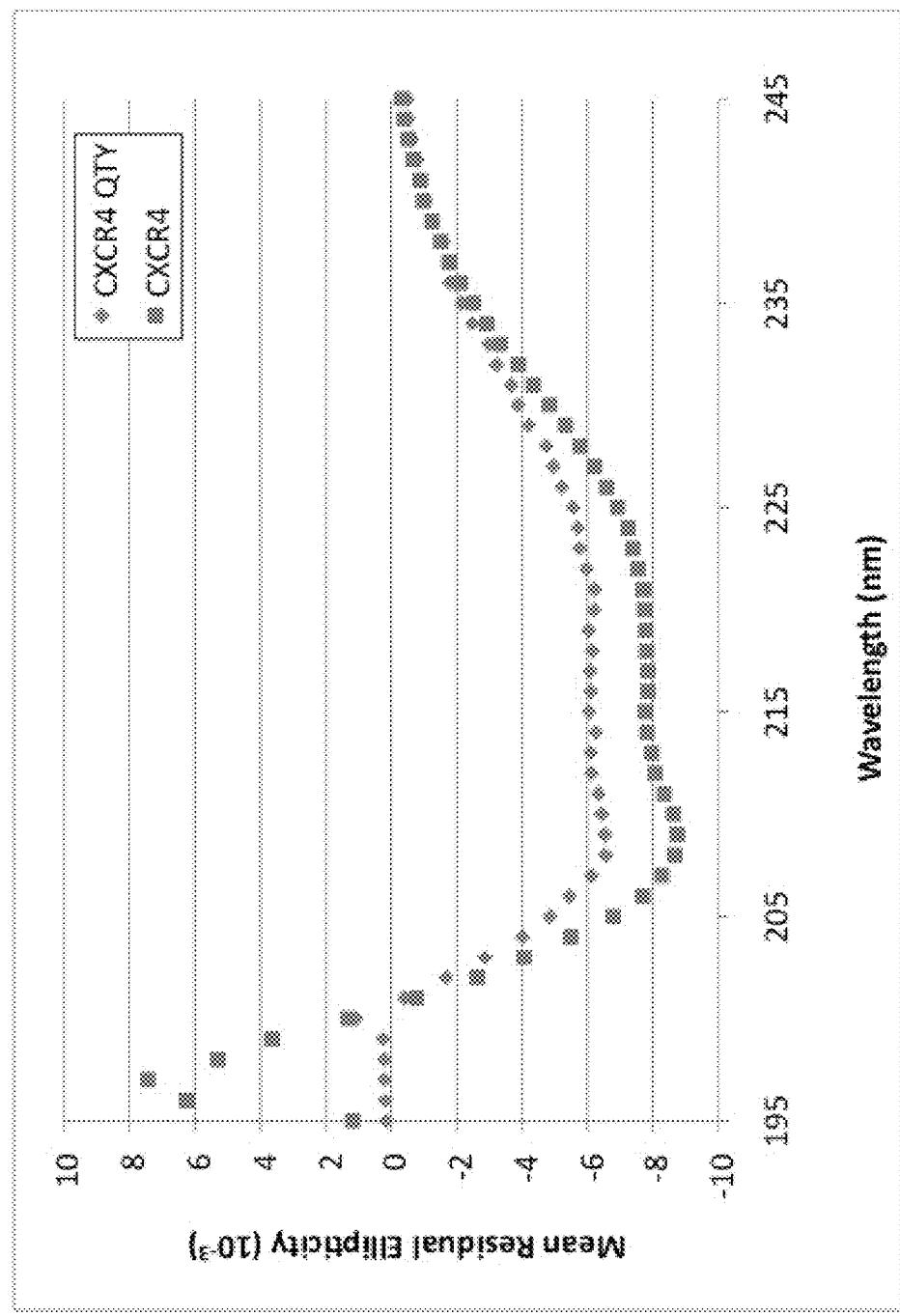
FIG. 4 Circular dichroism spectrum of CXCR4 and designed QTY mutation of CXCR4-QTY.
Figure 5:
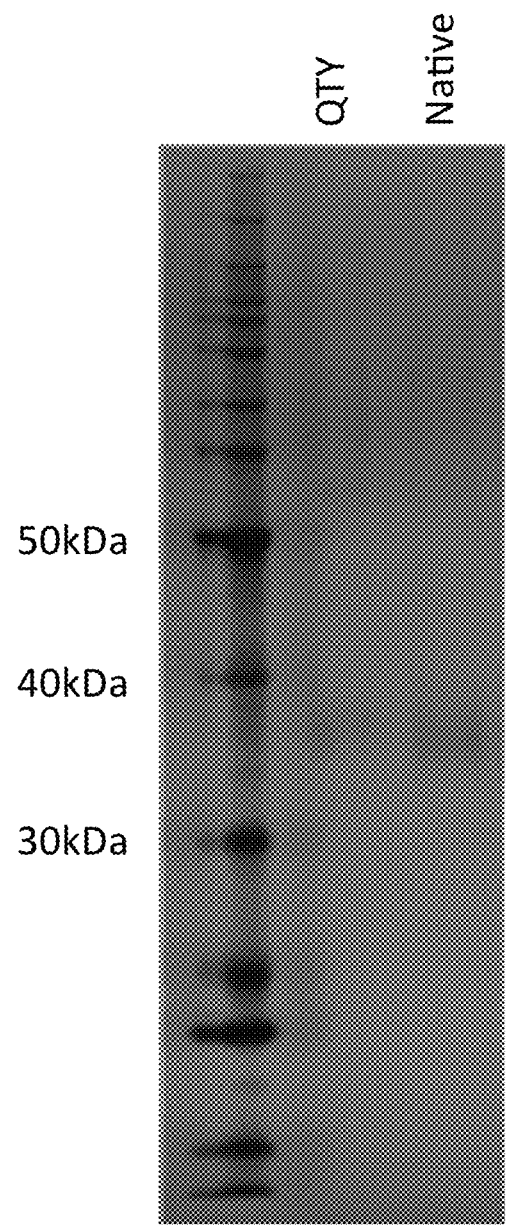
FIG. 5 SDS Gel showing comparison of molecular weight between native CXCR4 and CXCR4 with QTY mutations (SEQID NO:10: CXCR4 QTY).
Figure 6A:
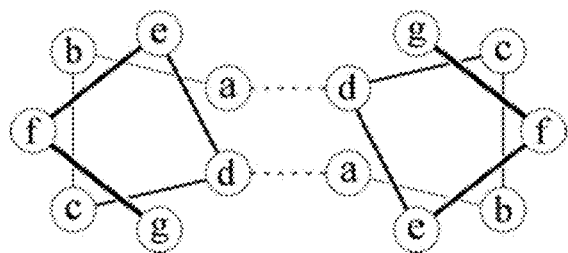
FIGS. 6A-6D show the use of QTY replacements to systematically mutate key residues on the 7-transmembrane alpha-helices and few other hydrophobic residues to convert the water-insoluble membrane form CXCR4 into a water-soluble form.
Figure 6B:
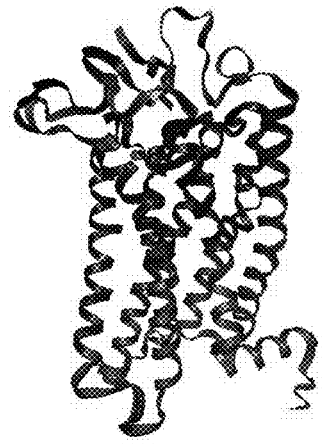
Figure 6C:
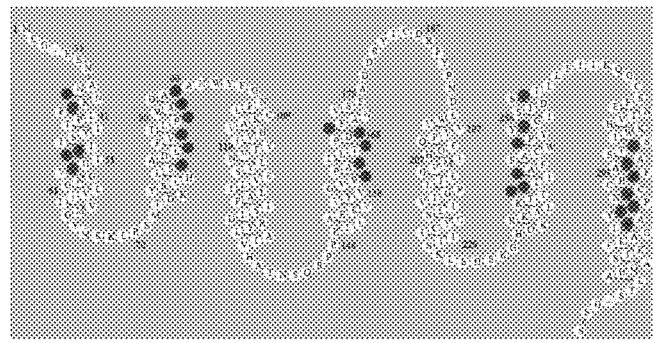
Figure 6D:
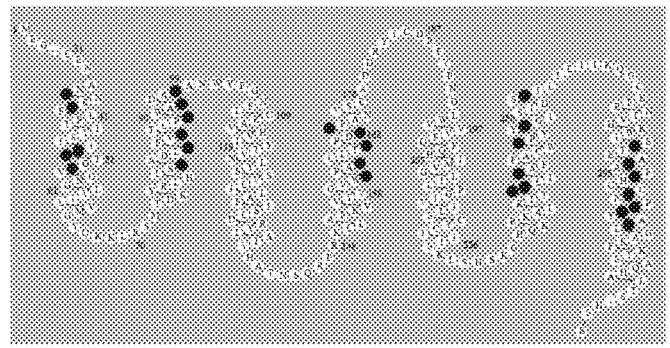

3) Determine secondary structure using circular dichroism. We can use circular dichroism (CD) spectral analysis to measure the secondary structures of the purified receptors. CD is a very sensitive technique that is be able to detect any small structural changes between the native and mutant receptors. Specifically, CD analysis can be used to calculate the percentage of α-helices and β-sheets in a protein. If a proteins' structure is altered, it can be revealed in the CD analysis. In addition to determining whether specific mutations alter receptor structure, CD can also be used to measure any odorant-induced structural changes. See FIG. 4

4) Assay ligand-binding of olfactory receptors. Microscale thermophoresis are used to measure the binding affinity of the native and bioengineered proteins and their odorant ligands. The key advantages of this technique over SPR or other ligand binding technologies are that they are totally surface-free and label free. Thus, the receptors do not need to be modified. The measurements can be performed in solution using native tryptophan as a signal source. Additionally, small ligands (MW ~200 Daltons) can be reliably measured. Furthermore, each measurement needs 0.5J.tl (1J1g/J.tl) of sample thus, save the precious receptor samples. These results show whether the mutant olfactory receptors are capable of binding odorants as efficiently as the native protein.

5) Use calcium influx activation assay to measure olfactory receptor activation. We can use calcium influx assays to examine odorant-induced activation of the native and variant olfactory receptors in HEK293 cells. This data is be correlated to the microscale thermophoresis measurements. Microscale thermophoresis directly measures ligand binding, while calcium influx assays measure activation. Combined, these assays can verify whether specific mutations affect binding, activation, or both. Additionally, we can distinguish between agonist and antagonist ligands.

6) Systematic screen for crystallization conditions. We can systematically screen the native and bioengineered variant olfactory receptors for crystallizing conditions in the absence and presence of odorants. The technology for crystallization screening of water-soluble proteins is well developed. Commercial screens are available which supply a variety of precipitants, salts, buffers with fine tuned pH gradients, and a range of cationic and anionic substances. All of these variables are well known and will be used in crystallizing membrane proteins. An additional unique ingredient of membrane protein screens is the presence of one of more detergent molecules. However, precipitation techniques involving slow water removal from the hanging drop may continue to be effective. Although it is useful to form large crystals, the results of a crystal screen may yield smaller crystals.

Surface Plasmon Resonance Analysis of CXCR4 QTY

Human CXCR4 and our CXCR4 QTY proteins obtained from cell-free production and purified with affinity beads were captured in different flow cells on a Biacore CM5 chip with immobilized 1D4 Antibody (Ab) in a Biacore 2000 instrument. Different concentrations of SDF1α, the native ligand for hCXCR4 receptor, were injected over the surface to allow interaction with the receptors.

```
HUMAN CXCR4 QTY
                                    (SEQ ID NO: 10)
MEGISIYTSDNYTEEMGSGDYDSMKEPCFREENANYNKTFLPTIYSIIYQ

TGTVGNGLVILVMGYQKKLRSMTDKYRLHLSTADLQFVTTLPYWATDATA

NWYFGNFLCKAVHVIYTVNLYSSVLILAFISLDRYLAIVHATNSQRPRKL

LAEKVVYVGVWTPAQLLTTPDYTFANVSEADDRYICDRFYPNDLWVVVFQ

FQHIMVGLILPGIVILSCYCIIISKLSHSKGHQKRKALKTTTTLIQAFFA

CWQPYYTGISIDSYILLEIIKQGCEFENTVHKWISTTEAQAFYHCCTNPT

QYAYLGAKFKTSAQHALTSVSRGSSLKILSKGKRGGHSSVSTESESSSSF

HS
```

Immobilization of 1D4 Antibody

Biacore CM5 chips were activated with 1-Ethyl-3-[3-dimethylaminopropyl]carbodiimide hydrochloride and N-hydroxysuccinimide according to the manufacturer's protocol prior to a 7 minute injection at 5 l/min of 1D4 Ab to flow cells 2-4 at 70 µg/ml followed by deactivating of the surfaces in all the 4 flow cells with a short Ethanolamine pulse. The immobilization level of 1D4 Ab range from 8000-25000 Response units (RU).

Capture of GPCRs

CXCR4 and CXCR4 QTY mutant are captured by the 1D4 Ab on the CM5 chip by injecting a 0.1 mg/ml sample of the protein to a single flow cell at 5 µl/min during 15 min with both sample and running buffer containing 0.2% Fos-Choline-14 detergent. The receptors were captured to a level of 800-3000 RU.

Interaction Analysis

SDF1α were injected over all flow cells to allow interaction with both the receptors and flow cell one is used as a reference cell without any immobilized protein. Injections were made at 0, 7.8 nM, 15.6 nM, 31.25 nM, 62.5 nM, 125 nM, 250 nM, 500 nM, 1 µM in triplicates, at 20 ul/min for 2 minutes with 15 min waiting time to allow dissociation. HBST (50 mM Hepes, pH 7.4, 150 mM NaCl, 0.005% Tween-20) with the addition of 0.2% BSA and 0.2% Fos-Choline-14 was used as both running buffer and for dilution of the SDF1α samples.

Conclusion: The above described study shows ligand binding by CXCR4 QTY.

REFERENCES

1. Choma C, Gratkowski H, Lear J D & DeGrado W F. (2000) Asparagine-mediated self-association of a model transmembrane helix. Nat Struct Biol 7, 161-6.
2. Slovic A M, Kono H, Lear J D, Saven J G & DeGrado W F. (2004) Computational design of water-soluble analogues of the potassium channel KcsA. Proc Natl Acad Sci USA 101, 1828-33.
3. Walters R F & DeGrado W F. (2006) Helix-packing motifs in membrane proteins. Proc Natl Acad Sci USA 103, 13658-63.
4. Zhang Y, Kulp D W, Lear J D & DeGrado W F. (2009) Experimental and computational evaluation of forces directing the association of transmembrane helices. J Am Chem Soc 131, 11341-11343.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a water-soluble variant of a G-protein coupled receptor (GPCR), the method comprising replacing residues leucine (L), isoleucine (I), valine (V), and phenylalanine (F) in hydrophilic surface α-helical positions b, c, and f but not positions a, d, e, and g within the 7-transmembrane α-helical domain of the GPCR with glutamine (Q), threonine (T), threonine (T), and tyrosine (Y), respectively, to produce the water-soluble variant of the GPCR, and synthesizing the water-soluble variant of the GPCR.

2. The method of claim 1, wherein the GPCR is an olfactory receptor.

3. The method of claim 2, wherein the GPCR is mOR103-15, or chemokine receptor CXCR4 (C-X-C chemokine receptor type 4).

4. The method of claim 1, wherein the GPCR is a mammalian protein.

5. The method of claim 1, further comprising determining the secondary structure of the GPCR.

6. The method of claim 5, wherein the secondary structure is determined using circular dichroism.

7. The method of claim 1, further comprising measuring ligand binding.

8. The method of claim 7, wherein ligand binding affinity of the water-soluble variant is compared to the native GPCR.

9. The method of claim 7, wherein the ligand binding is measured using microscale thermophoresis.

10. The method of claim 7, wherein the ligand binding is measured using a calcium influx assay.

11. The method of claim 1, wherein the GPCR is prepared using a cell-free system.

12. The method of claim 1, wherein the GPCR is an olfactory receptor and the method further comprising measuring odorant binding to the olfactory receptor.

13. The method of claim 1, wherein the GPCR is selected from the group consisting of: purinergic receptors, $M_1$ and $M_3$ muscarinic acetylcholine receptors, receptors for thrombin, receptors for thromboxane, receptors for sphingosine 1-phosphate, receptors for lysophosphatidic acid, receptors for angiotensin II, receptors for serotonin, receptors for somatostatin, receptors for endothelin, receptors for cholecystokinin, $V_{1a}$ vasopressin receptors, $D_5$ dopamine receptors, N-formylmethionine-leucyl-phenylalanine (fMLP) formyl peptide receptors, $GAL_2$ galanin receptors, $EP_3$ prostanoid receptors, $A_1$ adenosine receptors, $\alpha_1$ adrenergic receptors, $BB_2$ bombesin receptors, $B_2$ bradykinin receptors, calcium-sensing receptors, chemokine receptors, kaposi's sarcoma-associated herpesvirus-open reading frame 74 (KSHV-ORF74) chemokine receptors, $NK_1$ tachykinin receptors, thyroid-stimulating hormone (TSH) receptors, protease-activated receptors, neuropeptide receptors, adenosine A2B receptors, P2Y purinoceptors, metabolic glutamate receptors, G protein-coupled receptor kinase 5 (GRK5), GPCR-30, and CXCR4.

14. The method of claim 13, wherein:
(1) said purinergic receptors are selected from the group consisting of: $P2Y_1$, $P2Y_2$, $P2Y_4$, and $P2Y_6$;
(2) said receptors for thrombin are selected from the group consisting of: protease-activated receptor (PAR)-1, PAR-2;
(3) said receptors for thromboxane are receptors for thromboxane $A_2$ ($TXA_2$);
(4) said receptors for sphingosine 1-phosphate are selected from the group consisting of: receptors for $S1P_2$, receptors for $S1P_3$, receptors for $S1P_4$, and receptors for $S1P_5$;
(5) said receptors for lysophosphatidic acid are selected from the group consisting of: receptors for $LPA_1$, receptors for $LPA_2$, and receptors for $LPA_3$;
(6) said receptors for angiotensin II are angiotensin II $AT_1$ receptors;
(7) said receptors for serotonin are selected from the group consisting of: receptors for $5\text{-HT}_{2c}$, and receptors for $5\text{-HT}_4$;
(8) said receptors for somatostatin are somatostatin receptor type 5 (sst5) receptors;
(9) said receptors for endothelin are selected from the group consisting of: receptors for $ET_A$ and receptors for $ET_B$; or,
(10) said receptors for cholecystokinin are cholecystokinin A receptors ($CCK_1$).

15. The method according to claim 1, wherein at least 25 of said 7-transmembrane α-helical hydrophobic residues L, I, V, and F are replaced.

* * * * *

SEQUENCE LISTING

```
<160> NUMBER OF SEQ ID NOS: 10

<210> SEQ ID NO 1
<211> LENGTH: 340
<212> TYPE: PRT
<213> ORGANISM: Artificial Sequence
<220> FEATURE:
<223> OTHER INFORMATION: Synthetic

<400> SEQUENCE: 1
```

Met Glu Arg Arg Asn His Thr Gly Arg Val Ser Glu Phe Val Leu Leu
1               5                   10                  15

Gly Phe Pro Ala Pro Ala Leu Arg Ala Leu Leu Phe Phe Leu Leu Ser
            20                  25                  30

Leu Leu Ala Tyr Val Leu Val Leu Thr Glu Asn Ile Leu Ile Thr Ala
            35                  40                  45

Ile Arg Asn His Pro Thr Leu His Lys Pro Met Tyr Phe Phe Leu Ala
        50                  55                  60

Asn Met Ser Glu Phe Leu Glu Ile Trp Tyr Val Thr Val Thr Ile Pro
65                  70                  75                  80

Lys Met Leu Ala Gly Phe Ile Gly Ser Glu Glu Asn His Gly Gln Leu
                85                  90                  95

Ile Ser Phe Glu Ala Cys Met Thr Gln Leu Tyr Phe Phe Leu Gly Leu
            100                 105                 110

Gly Cys Thr Glu Cys Val Leu Leu Ala Val Met Ala Tyr Asp Arg Tyr
        115                 120                 125

Val Ala Ile Cys His Pro Leu His Tyr Pro Val Ile Val Ser Ser Arg
        130                 135                 140

Leu Cys Val Gln Met Ala Ala Gly Ser Trp Ala Gly Gly Phe Gly Ile
145                 150                 155                 160

Ser Met Val Lys Val Phe Leu Ile Ser Arg Leu Tyr Thr Cys Gly Pro
                165                 170                 175

Asn Thr Ile Asn His Phe Phe Cys Asp Val Ser Pro Leu Leu Asn Leu
            180                 185                 190

Ser Cys Thr Asp Met Ser Thr Ala Glu Leu Thr Asp Phe Ile Leu Ala
        195                 200                 205

Ile Phe Ile Leu Leu Gly Pro Leu Ser Val Thr Gly Ala Ser Tyr Met
        210                 215                 220

Ala Ile Thr Gly Ala Val Met Arg Ile Pro Ser Ala Ala Gly Arg His
225                 230                 235                 240

Lys Ala Phe Ser Thr Cys Ala Ser His Leu Thr Val Val Ile Ile Phe
                245                 250                 255

Tyr Ala Ala Ser Ile Phe Ile Tyr Ala Arg Pro Lys Ala Leu Ser Ala
            260                 265                 270

Phe Asp Thr Asn Lys Leu Val Ser Val Leu Tyr Ala Val Ile Val Pro
        275                 280                 285

Leu Leu Asn Pro Ile Ile Tyr Cys Leu Arg Asn Gln Glu Val Lys Lys
        290                 295                 300

Ala Leu Arg Arg Thr Leu His Leu Ala Gln Gly Gln Asp Ala Asn Thr
305                 310                 315                 320

Lys Lys Ser Ser Arg Asp Gly Gly Ser Ser Gly Thr Glu Thr Ser Gln
                325                 330                 335

Val Ala Pro Ala
        340

<210> SEQ ID NO 2
<211> LENGTH: 341
<212> TYPE: PRT
<213> ORGANISM: Artificial Sequence
<220> FEATURE:
<223> OTHER INFORMATION: Synthetic

<400> SEQUENCE: 2

Met Glu Arg Arg Asn His Thr Gly Arg Val Ser Glu Phe Val Leu Leu
1               5                   10                  15

-continued

Gly Phe Pro Ala Pro Ala Pro Gln Arg Ala Leu Gln Phe Phe Gln Ser
            20                  25                  30

Leu Gln Ala Tyr Val Gln Thr Leu Thr Glu Asn Ile Gln Thr Ile Thr
        35                  40                  45

Ala Ile Arg Asn His Pro Thr Leu His Lys Pro Met Tyr Tyr Phe Leu
    50                  55                  60

Ala Asn Met Ser Phe Tyr Leu Glu Thr Trp Tyr Thr Thr Val Thr Thr
65                  70                  75                  80

Pro Lys Met Gln Ala Gly Tyr Ile Gly Ser Glu Asn His Gly Gln
                85                  90                  95

Leu Ile Ser Phe Glu Ala Cys Met Thr Gln Leu Tyr Phe Gln Gly
            100                 105                 110

Leu Gly Cys Thr Glu Cys Thr Leu Leu Ala Val Met Ala Tyr Asp Arg
            115                 120                 125

Tyr Val Ala Thr Cys His Pro Leu His Tyr Pro Val Ile Val Ser Ser
    130                 135                 140

Arg Gln Cys Val Gln Met Ala Ala Gly Ser Trp Ala Gly Gly Phe Gly
145                 150                 155                 160

Thr Ser Met Thr Val Lys Val Tyr Gln Ile Ser Arg Leu Ser Tyr Cys
                165                 170                 175

Gly Pro Asn Thr Ile Asn His Phe Phe Cys Asp Val Ser Pro Leu Leu
            180                 185                 190

Asn Leu Ser Cys Thr Asp Met Ser Thr Ala Glu Leu Thr Asp Phe Ile
        195                 200                 205

Leu Ala Ile Phe Ile Leu Leu Gly Pro Leu Ser Val Thr Gly Ala Ser
    210                 215                 220

Tyr Met Ala Ile Thr Gly Ala Val Met Arg Ile Pro Ser Ala Ala Gly
225                 230                 235                 240

Arg His Lys Ala Phe Ser Thr Cys Ala Ser His Leu Thr Thr Val Ile
                245                 250                 255

Thr Tyr Tyr Ala Ala Ser Ile Tyr Thr Tyr Ala Arg Pro Lys Ala Leu
            260                 265                 270

Ser Ala Phe Asp Thr Asn Lys Leu Val Ser Val Leu Tyr Ala Val Ile
        275                 280                 285

Val Pro Leu Leu Asn Pro Ile Ile Tyr Cys Leu Arg Asn Gln Glu Val
    290                 295                 300

Lys Lys Ala Leu Arg Arg Thr Leu His Leu Ala Gln Gly Asp Ala Asn
305                 310                 315                 320

Thr Lys Lys Ser Ser Arg Asp Gly Gly Ser Ser Gly Thr Glu Thr Ser
                325                 330                 335

Gln Val Ala Pro Ala
            340

<210> SEQ ID NO 3
<211> LENGTH: 29
<212> TYPE: PRT
<213> ORGANISM: Artificial Sequence
<220> FEATURE:
<223> OTHER INFORMATION: Synthetic

<400> SEQUENCE: 3

Pro Gln Arg Ala Leu Gln Phe Phe Gln Ser Leu Gln Ala Tyr Val Gln
1               5                   10                  15

Thr Leu Thr Glu Asn Ile Gln Thr Ile Thr Ala Ile Arg
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic

<400> SEQUENCE: 4

Met Tyr Tyr Phe Leu Ala Asn Met Ser Phe Tyr Leu Glu Thr Trp Tyr
1               5                   10                  15

Thr Thr Val Thr Thr Pro Lys Met Gln Ala Gly Tyr Ile
            20                  25

<210> SEQ ID NO 5
<211> LENGTH: 31
<212> TYPE: PRT
<213> ORGANISM: Artificial Sequence
<220> FEATURE:
<223> OTHER INFORMATION: Synthetic

<400> SEQUENCE: 5

Cys Met Thr Gln Leu Tyr Phe Phe Gln Gly Leu Gly Cys Thr Glu Cys
1               5                   10                  15

Thr Leu Leu Ala Val Met Ala Tyr Asp Arg Tyr Val Ala Thr Cys
            20                  25                  30

<210> SEQ ID NO 6
<211> LENGTH: 25
<212> TYPE: PRT
<213> ORGANISM: Artificial Sequence
<220> FEATURE:
<223> OTHER INFORMATION: Synthetic

<400> SEQUENCE: 6

Arg Gln Cys Val Gln Met Ala Ala Gly Ser Trp Ala Gly Gly Phe Gly
1               5                   10                  15

Thr Ser Met Thr Val Lys Val Tyr Gln
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic

<400> SEQUENCE: 7

Leu Thr Asp Phe Ile Leu Ala Ile Phe Ile Leu Leu Gly Pro Leu Ser
1               5                   10                  15

Val Thr Gly Ala Ser Tyr Met Ala Ile Thr Gly Ala Val
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic

<400> SEQUENCE: 8

His Lys Ala Phe Ser Thr Cys Ala Ser His Leu Thr Thr Val Ile Thr
1               5                   10                  15

Tyr Tyr Ala Ala Ser Ile Tyr Thr Tyr 20                  25

<210> SEQ ID NO 9
<211> LENGTH: 25
<212> TYPE: PRT
<213> ORGANISM: Artificial Sequence
<220> FEATURE:
<223> OTHER INFORMATION: Synthetic

<400> SEQUENCE: 9

Thr Asn Lys Leu Val Ser Val Leu Tyr Ala Val Ile Val Pro Leu Leu
 1               5                  10                  15

Asn Pro Ile Ile Tyr Cys Leu Arg Asn
            20                  25

<210> SEQ ID NO 10
<211> LENGTH: 352
<212> TYPE: PRT
<213> ORGANISM: Artificial Sequence
<220> FEATURE:
<223> OTHER INFORMATION: Synthetic

<400> SEQUENCE: 10

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
            20                  25                  30

Asn Ala Asn Tyr Asn Lys Thr Phe Leu Pro Thr Ile Tyr Ser Ile Ile
         35                  40                  45

Tyr Gln Thr Gly Thr Val Gly Asn Gly Leu Val Ile Leu Val Met Gly
     50                  55                  60

Tyr Gln Lys Lys Leu Arg Ser Met Thr Asp Lys Tyr Arg Leu His Leu
 65                  70                  75                  80

Ser Thr Ala Asp Leu Gln Phe Val Thr Leu Pro Tyr Trp Ala Thr
                 85                  90                  95

Asp Ala Thr Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Thr Pro Ala Gln Leu Leu Thr Thr Pro Asp Tyr Thr Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Thr Thr Leu Ile Gln Ala Phe Phe Ala Cys Trp Gln Pro Tyr Tyr
                245                 250                 255

Thr Gly Ile Ser Ile Asp Ser Tyr Ile Leu Leu Glu Ile Ile Lys Gln
            260                 265                 270

-continued

```
Gly Cys Glu Phe Glu Asn Thr Val His Lys Trp Ile Ser Thr Thr Glu
        275                 280                 285
Ala Gln Ala Phe Tyr His Cys Cys Thr Asn Pro Thr Gln Tyr Ala Tyr
        290                 295                 300
Leu Gly Ala Lys Phe Lys Thr Ser Ala Gln His Ala Leu Thr Ser Val
305                 310                 315                 320
Ser Arg Gly Ser Ser Leu Lys Ile Leu Ser Lys Gly Lys Arg Gly Gly
                325                 330                 335
His Ser Ser Val Ser Thr Glu Ser Glu Ser Ser Ser Ser Phe His Ser
                340                 345                 350
```